United States Patent
LeJeune et al.

(10) Patent No.: US 6,290,914 B1
(45) Date of Patent: Sep. 18, 2001

(54) FRAGRANCE RING FOR OIL LAMPS

(75) Inventors: Gene M. LeJeune, Slinger; Jon C. Gallun, Waukesha; Ray A. Millikin, Sussex; Annette R. Schmitt, West Bend, all of WI (US)

(73) Assignee: Lamplight Farms, Inc., Menomonee Falls, WI (US)

( * ) Notice: Subject to any disclaimer, the term of this patent is extended or adjusted under 35 U.S.C. 154(b) by 0 days.

(21) Appl. No.: 09/689,535

(22) Filed: Oct. 11, 2000

(51) Int. Cl.[7] ........................................... A62B 7/08

(52) U.S. Cl. ........................ 422/125; 422/5; 422/123; 422/125; 422/307

(58) Field of Search .................. 422/5, 123, 125, 422/307

(56) References Cited

U.S. PATENT DOCUMENTS

| | | | | |
|---|---|---|---|---|
| 729,019 | * | 5/1903 | Valentine | 422/125 |
| 2,254,906 | * | 9/1941 | Petrullis | 422/125 |
| 4,781,895 | * | 11/1988 | Spector | 422/125 |
| 5,840,246 | * | 11/1998 | Hammons et al. | 422/125 |

FOREIGN PATENT DOCUMENTS

3768 * 12/1899 (EP) .

* cited by examiner

Primary Examiner—Robert J. Warden, Sr.
Assistant Examiner—Imad Soubra
(74) Attorney, Agent, or Firm—Donald J. Ersler

(57) ABSTRACT

A fragrance ring includes a fragrance holder and a quantity of liquid scent. The fragrance holder includes a rim portion attached to a top of a body portion to form a fragrance trough. The body portion is received by a chimney retainer of an oil lamp and the body portion receives a glass chimney. The fragrance trough is filled with the liquid scent. An oil lamp flame causes the liquid scent to evaporate and emit a pleasant aroma. In a second embodiment, the fragrance ring includes a snap-on trough ring and a liquid scent. A snap-on area is formed on an inside perimeter of the snap-on trough ring at a bottom thereof. The snap-on trough is snapped on to a top of a chimney retainer to secure the snap-on trough ring thereto. The snap-on trough ring is filled with the liquid scent. The oil lamp flame causes the liquid scent to evaporate and emit a pleasant aroma. In a third embodiment, the fragrance ring includes a trough ring, trough ring retainer, and a solid scent mixture. The trough ring retainer is inserted into the chimney retainer of the oil lamp. The trough ring is inserted into a ring trough formed in the trough ring retainer. The solid scent mixture includes a liquid scent mixed with a candle wax. The oil lamp flame causes the solid scent mixture to melt and evaporate.

3 Claims, 4 Drawing Sheets

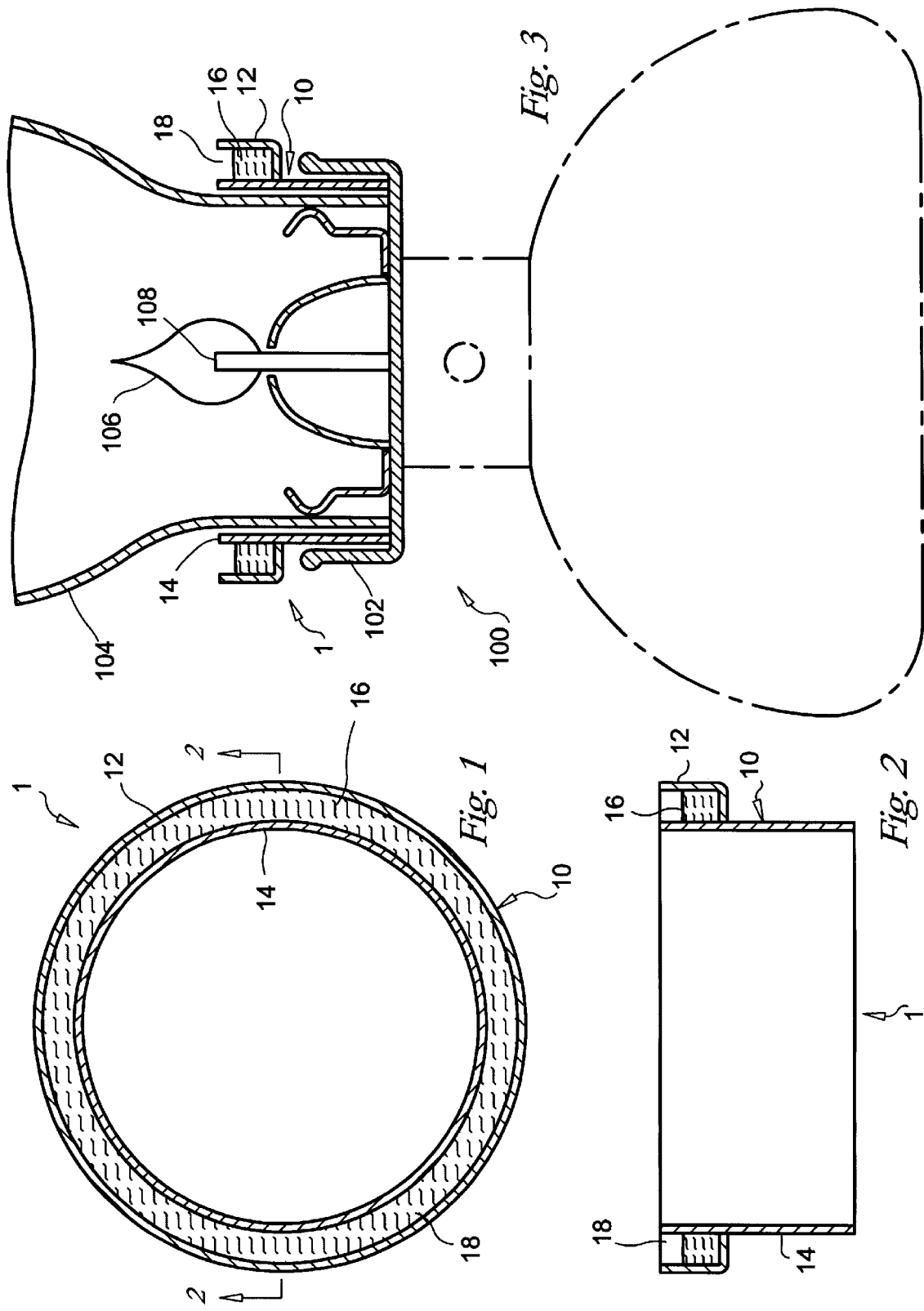

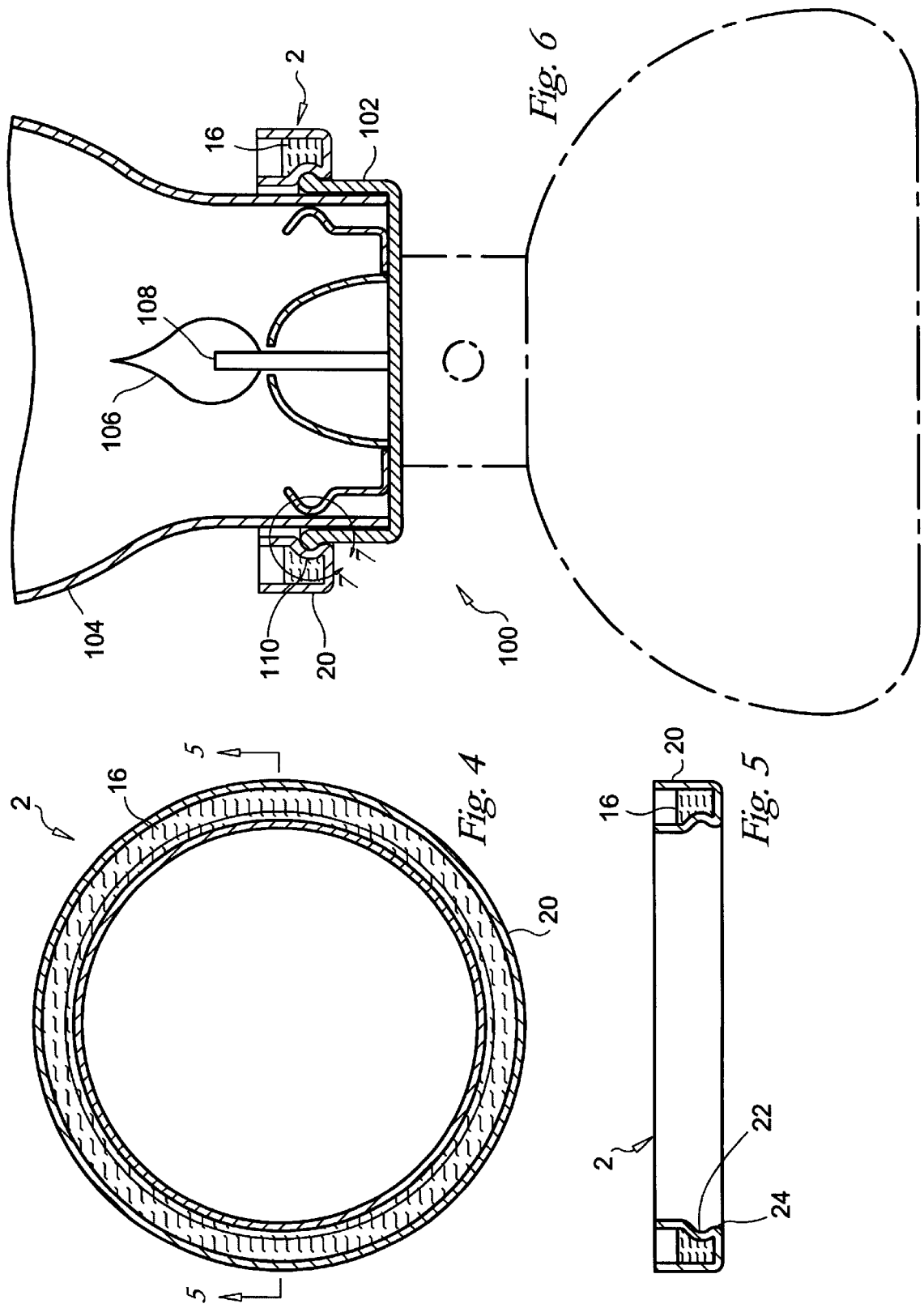

FRAGRANCE RING FOR OIL LAMPS

BACKGROUND OF THE INVENTION

1. Field of the Invention

The present invention relates generally to oil lamps and more specifically to a fragrance ring for oil lamps which may be attached to an oil lamp to provide a pleasant scent when the oil lamp is burning.

2. Discussion of the Prior Art

There have been some attempts at making an oil lamp which emits a scent while burning. One attempt was to mix a liquid scent with in the lamp oil. However, the scent solution ended up being burned without emitting an aroma. Another attempt was to use a U-shaped cross sectional ring which was placed on the glass chimney of the oil lamp. The ring was filled with a liquid scent. The drawback to the U-shaped cross sectional ring design is that when the glass chimney of the oil lamp is removed the ring must be removed or the fragrance will spill out.

Accordingly, there is a clearly felt need in the art for a fragrance ring for oil lamps which may be securely attached to an existing oil lamp to provide a pleasant scent when the oil lamp is burning.

SUMMARY OF THE INVENTION

The present invention provides a fragrance ring which allows a pleasant scent to be emitted from the oil lamp when thereof is burning. The fragrance ring includes a fragrance holder and a liquid scent. The fragrance holder includes a rim portion and a body portion. The body portion is sized to be received by a chimney retainer. The rim portion is attached to an outside perimeter of the body portion at a top thereof to form a fragrance trough. The fragrance trough is substantially at the same height as a flame generated at the wick. An inside perimeter of the body portion is sized to slidably receive the outer perimeter of the glass chimney. The fragrance trough is filled with the liquid scent. The flame causes the quantity of scent to evaporate and emit a pleasant aroma.

In a second embodiment, the fragrance ring includes a snap-on trough ring and a liquid scent. A depressed area is formed on an inside perimeter of the snap-on trough ring at a bottom thereof. The depressed area is sized to receive a finishing lip at a top of the chimney retainer. A retention lip is formed at a bottom of the depressed area. The retention lip snaps below the finishing lip to securely retain the snap-on trough ring on the chimney retainer. The snap-on trough ring is at substantially the same height as the flame when attached to the chimney retainer. The snap-on trough ring is filled with the liquid scent. The flame causes the liquid scent to evaporate and emit a pleasant aroma.

In a third embodiment, the fragrance ring includes a trough ring, a trough ring retainer, and a solid scent mixture. The trough ring retainer is inserted into the chimney retainer of the oil lamp. The trough ring is inserted into a ring trough formed in the trough ring retainer. It is preferable that the ring trough be at substantially the same height as the flame. The solid scent mixture includes a liquid scent mixed with a candle wax. The solid scent mixture is poured into the trough ring while still liquid and allowed to solidify. The solid scent mixture will melt and evaporate from the heat of the flame. When the flame is extinguished, the solid scent mixture resolidifies.

Accordingly, it is an object of the present invention to provide a fragrance ring which allows an oil lamp to emit a pleasant aroma while burning.

It is a further object of the present invention to provide a fragrance ring which may be securely attached to an existing oil lamp.

Finally, it is another object of the present invention to provide a fragrance ring which is disposable.

These and additional objects, advantages, features and benefits of the present invention will become apparent from the following specification.

BRIEF DESCRIPTION OF THE DRAWINGS

FIG. 1 is a top view of a fragrance ring in accordance with the present invention.

FIG. 2 is a cross sectional view of a fragrance ring lamps in accordance with the present invention.

FIG. 3 is a cross sectional view of a fragrance ring attached to an oil lamp in accordance with the present invention.

FIG. 4 is a top view of a second embodiment of a fragrance ring in accordance with the present invention.

FIG. 5 is a cross sectional view of a second embodiment of a fragrance ring in accordance with the present invention.

FIG. 6 is a cross sectional view of a second embodiment of a fragrance ring attached to an oil lamp in accordance with the present invention.

DETAILED DESCRIPTION OF THE PREFERRED EMBODIMENTS

Figures 7, 12:
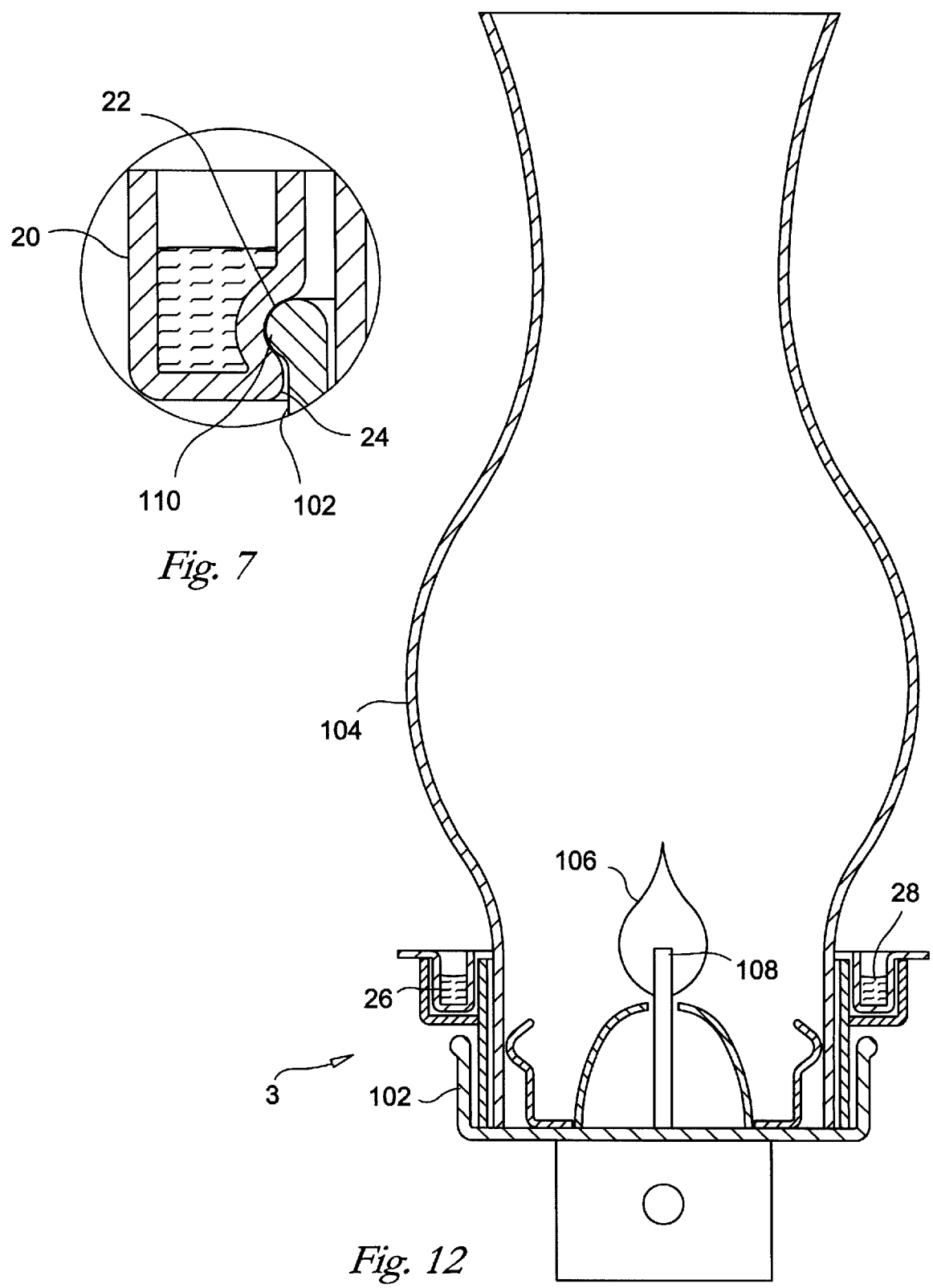
FIG. 7 is an enlarged cross sectional view of a second embodiment of a fragrance ring retained by a finishing lip of a glass chimney retainer in accordance with the present invention.
FIG. 12 is a cross sectional view of a third embodiment of a fragrance ring attached to an oil lamp in accordance with the present invention.

With reference now to the drawings, and particularly to FIG. 1, there is shown a top view of fragrance ring 1. With reference to FIGS. 2–3, the fragrance ring 1 includes a fragrance holder 10 and a quantity of liquid scent 16. The fragrance holder 10 includes a rim portion 12 and a body portion 14. An outer perimeter of the body portion 14 is sized to slidably fit into a chimney retainer 102 of an oil lamp 100. An inner perimeter of the body portion 14 is sized to slidably receive a glass chimney 104. The rim portion 12 is attached to an outside perimeter of the body portion 14 at a top thereof to form a fragrance trough 18. The rim portion 12 may be attached to the body portion 14 by metal spinning, adhesive, welding, or any other suitable assembly process. The rim portion 12 and the body portion 14 may also be fabricated from a single piece of material. The fragrance trough 18 is substantially the same height as a flame 106 generated at the wick 108. The fragrance trough 18 is filled with the liquid scent 16 from an eye dropper or any other suitable device. The flame 106 causes the liquid scent 16 to evaporate and emit a pleasant aroma. A liquid scent 16 has been shown and described, but a solid scent mixture could also be used.

With reference to FIGS. 4–7, a second embodiment of the fragrance ring 2 includes a snap-on trough ring 20 and the liquid scent 16. The snap-on trough ring 20 includes an inside wall and an outside continuous wall extending upward from a bottom surface. A depressed area 22 is formed on an inside perimeter (wall) of the snap-on trough ring 20 at a bottom thereof. A retention lip 24 is formed at a bottom of the depressed area 22. The depressed area 22 is sized to receive a finishing lip 110 at a top of the glass chimney retainer 102. The retention lip 110 snaps below the finishing lip 110 to securely retain the snap-on trough ring 20 on the chimney retainer 102. The snap-on trough ring 20 is at substantially the same height as the flame 106 generated by the wick 108 when attached to the glass chimney retainer 102. The snap-on trough ring 20 is filled with the liquid scent from an eye dropper or any other suitable device. The flame 106 causes the liquid scent to evaporate and emit a pleasant aroma. A liquid scent 16 has been shown and described, but a solid scent mixture could also be used.

Figure 8:
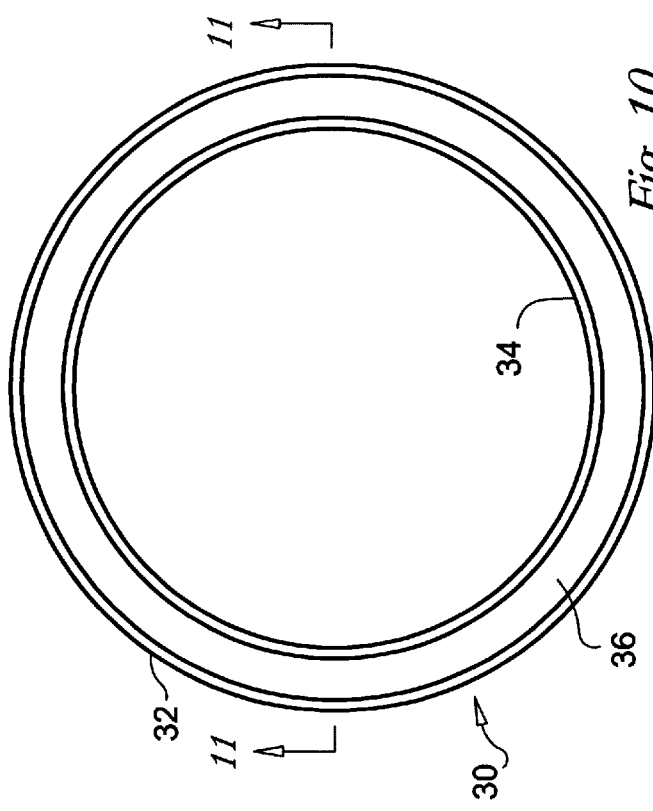
FIG. 8 is a top view of a trough ring of a third embodiment of a fragrance ring in accordance with the present invention.
Figure 9:
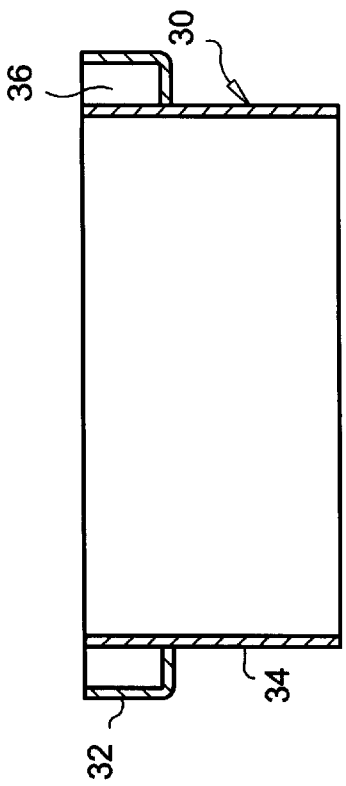
FIG. 9 is a cross sectional view of a trough ring of a third embodiment of a fragrance ring in accordance with the present invention.
Figure 10:
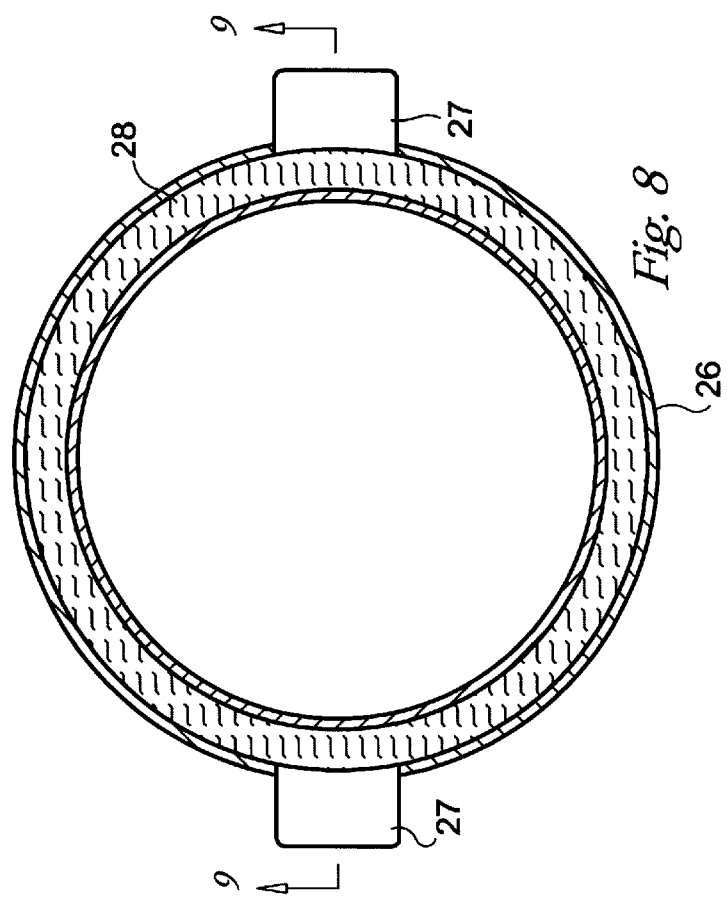
FIG. 10 is a top view of a trough ring retainer of a third embodiment of a fragrance ring in accordance with the present invention.
Figure 11:
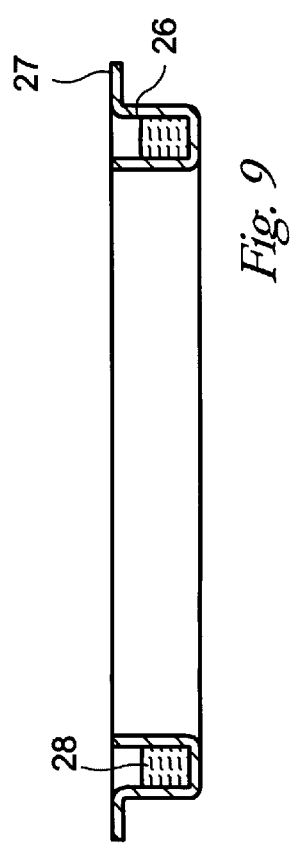
FIG. 11 is a cross sectional view of a trough ring retainer of a third embodiment of a fragrance ring in accordance with the present invention.

With reference to FIGS. 8–10, a third embodiment of the fragrance ring 3 includes a trough ring 26, a trough ring retainer 30, and a solid scent mixture 28. The trough ring 26 includes an inside wall and outside continuous wall extending upward from a bottom surface. A pair of opposing tabs 27 preferably extend outward from a top of the trough ring 26. The trough ring retainer 30 includes a rim portion 32 and a body portion 34. An outer perimeter of the body portion 34 is sized to slidably fit into a chimney retainer 102 of an oil lamp 100. An inner perimeter of the body portion 34 is sized to slidably receive a glass chimney 104. The rim portion 32 is attached to an outside perimeter of the body portion 34 at a top thereof to form a ring trough 36. The ring trough 36 is sized to receive the trough ring 26.

The rim portion 32 may be attached to the body portion 34 by metal spinning, adhesive, welding, or any other suitable assembly process. The rim portion 32 and the body portion 34 may also be fabricated from a single piece of material. The ring trough 36 is substantially at the same height as a flame 106 generated at the wick 108. The solid scent mixture 28 includes a liquid scent mixed with a candle wax. The solid scent mixture 28 is poured into the trough ring 26 while still liquid and allowed to solidify by the manufacturer. The solid scent mixture 28 will melt and evaporate from the heat of the flame 106, giving off a fragrance. When the flame 106 is extinguished, the solid scent mixture resolidifies. The trough ring 26 is preferably fabricated from a disposable material.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

What is claimed is:

1. A fragrance ring for attachment to an oil lamp comprising:

a snap-on trough ring having an inside wall and an outside wall extending upward from a bottom surface, a depressed area being formed on said inside wall at a bottom thereof, an inside wall of said snap-on trough ring being sized to receive an outside wall of a glass chimney;

an oil lamp having a chimney retainer, a finishing lip being formed on a top of the chimney retainer, said depressed area being sized to receive the finishing lip, a height of said fragrance trough being retained at substantially the same height as an oil lamp flame; and a solid scent mixture being contained in said fragrance trough, said solid scent mixture including a liquid scent mixed with a candle wax, wherein the oil lamp flame causing said candle wax to melt and said liquid scent to vaporize.

2. The fragrance ring for attachment to an oil lamp of claim 1, further comprising:

a retention lip being formed on a bottom of said depressed area, said retention lip snapping below the finishing lip to securely retain said trough ring on the chimney retainer.

3. A fragrance ring for attachment to an oil lamp comprising:

a snap-on trough ring having an inside wall and an outside wall extending upward from a bottom surface, a depressed area being formed on said inside wall at a bottom thereof, a retention lip being formed on a bottom of said depressed area, said retention lip snapping below the finishing lip to securely retain said trough ring on the chimney retainer, an inside wall of said snap-on trough ring being sized to receive an outside wall of a glass chimney;

an oil lamp having a chimney retainer, a finishing lip being formed on a top of the chimney retainer, said depressed area being sized to receive the finishing lip, a height of said fragrance trough being retained at substantially the same height as an oil lamp flame; and a solid scent mixture being contained in said fragrance trough, said solid scent mixture including a liquid scent mixed with a candle wax, wherein the oil lamp flame causing said candle wax to melt and said liquid scent to vaporize.

* * * * *